United States Patent [19]

Hashimoto et al.

[11] 3,950,450

[45] Apr. 13, 1976

[54] PROCESS FOR PRODUCING 4-METHYL-1-PENTENE

[75] Inventors: Harukichi Hashimoto; Shuichi Omiya, both of Sendai, Japan

[73] Assignee: Idemitsu Petrochemical Co., Ltd., Tokyo, Japan

[22] Filed: July 12, 1974

[21] Appl. No.: 488,180

[30] Foreign Application Priority Data
July 12, 1973   Japan.............................. 48-77901

[52] U.S. Cl. ...................... 260/683.15 E; 252/430
[51] Int. Cl.² .......................................... C07C 3/20
[58] Field of Search ........................... 260/683.15 E

[56] References Cited
UNITED STATES PATENTS 3,251,895   5/1966   Wilkes........................ 260/683.15 E
3,375,294   3/1968   Beavers...................... 260/683.15 E
3,755,491   8/1973   Hashimoto ................. 260/683.15 E Primary Examiner—Paul M. Coughlan, Jr.
Attorney, Agent, or Firm—Armstrong, Nikaido & Wegner

[57]   ABSTRACT

Propylene is dimerized in the present of a catalyst composed of potassium, copper and an aliphatic tertiary amine. The dimerization is carried out in an inert gas atmosphere, at 150° – 200°C., and in the substantial absence of oxygen and water, 4-methyl-1-pentene is produced with high selectivity.

3 Claims, No Drawings

PROCESS FOR PRODUCING 4-METHYL-1-PENTENE

This invention relates to a novel process for producing 4-methyl-1-pentene by dimerizing propylene.

More particularly, the invention pertains to a process for synthesizing 4-methyl-1-pentene with high selectivity by dimerizing propylene in the presence of a novel catalyst composed of potassium, copper and an aliphatic tertiary amine.

As to the dimerization reaction of propylene, there has heretofore been known a process of this inventor using a catalyst composed of (a) potassium or a potassium-sodium mixture and (b) a metal selected from the group consisting of copper, silver and magnesium (Japanese Pat. No. 645,565). According to the above-mentioned process, however, the reaction rate is low, and for example, where the reaction is effected in a heptane solvent at 180°C for 5 hours, the conversion of propylene is not more than 15% and the selectivity for 4-methyl-1-pentene is at most 87%. The selectivity for 4-methyl-1-pentene referred to herein means the content (% by weight) of 4-methyl-1-pentene in the resulting propylene dimers, i.e. $C_6$ - olefins. Further, I have disclosed a process using a potassium-copper catalyst which has previously been heat-treated in an aliphatic hydrocarbon solvent in an inert atmosphere in the presence or absence of propylene (Japanese Pat. No. 656,359). According to the said process, the reaction rate of propylene increases, but the selectivity for 4-methyl-1-pentene cannot be enhanced and there is observed that the selectivity for 4-methyl-1-pentene is decreased if the conversion of propylene is increased.

Further, according to my invention (U.S. Pat. No. 3,755,491, British Pat. No. 1,338,190 corresponding to Japanese Patent Application No. 11871/72) using a process for producing 4-methyl-1-pentene by dimerizing propylene in the presence of a catalyst composed of (a) potassium (b) copper and (c) potassium alkoxides derived from aliphatic saturated primary or secondary alcohols, the selectivity for 4-methyl-1-pentene can be increased and, in particular cases, the reaction rate of propylene can be increased more than in the conventional process. Therefore, an object of the present invention is to provide a novel process remarkably increasing the reaction rate of propylene and maintaining the high selectivity for 4-methyl-1-pentene by dimerizing propylene in the presence of a new catalyst composed of potassium, copper and an aliphatic tertiary amine.

I have now found that when a catalyst prepared by adding an aliphatic tertiary amine to a mixture of potassium and copper is used, the reaction rate of propylene can be increased more than when using the above-mentioned catalyst composed of potassium and copper, and, in particular cases, more than when using the above-mentioned catalyst composed of potassium, copper and a potassium alkoxide, and the high selectivity for 4-methyl-1-pentene can be maintained, in general, at about 90%. I have further found that the above-mentioned high selectivity for 4-methyl-1-pentene can be maintained even when the conversion of propylene is 50% or more, and in particular cases 75%. In the new catalyst of the present invention composed of the three components, each component is essential, and the catalyst is not effective if one of them is absent.

The aliphatic tertiary amines useful in the present invention include aliphatic saturated tertiary amines having 3 to 30 carbon atoms. The tertiary amines include acyclic and cyclic monoamines and diamines.

Examples of such aliphatic tertiary amines in the present invention include trimethylamine, triethylamine, tripropylamine, tributylamine, trihexylamine, trioctylamine, N-methylpyrrolidine, N-methylpiperidine, N,N,N'n,'-tetramethyl-ethylenediamine and 1,4-diazabicyclo [2.2.2] octane (i.e. triethylenediamine).

Aliphatic primary or secondary amines are not effective for use in the present invention.

In the present invention, the aliphatic tertiary amine is used in a proportion of 0.1 to 5 moles, preferably 0.2 to 2 moles, per mole of the potassium used as a catalyst component. The reaction of dimerizing propylene in the presence of the catalyst according to the present invention is carried out in a nitrogen or like inert gas atmosphere at 150° to 200°C., preferably at about 180°C., and generally, in the substantial absence of oxygen and water.

The present invention is illustrated in further detail hereinbelow with reference to the examples.

EXAMPLE 1

A mixture comprising 70 ml. of refined heptane free of water, 2.0 g. of potassium, 3.2 g. of copper powder and 9.0 g. of N-methyl piperidine was fed to a 300 ml. stainless steel electromagnetic stirring type autoclave.

The autoclave was closed and the air in the autoclave was substituted with nitrogen.

Subsequently, 68 g. of propylene was introduced under pressure into the autoclave and then reacted at 180°C. for 1.4 hours. After unreacted propylene was removed, the reaction liquid in the autoclave was recovered and tested by means of gas chromatography. As a result, the conversion of propylene was determined to be 75% and the selectivity for 4-methyl-1-pentene was 91%.

As to other main products, the selectivity for 4-methyl-2-pentene was 4% and the selectivity for the total of 1-herene and 2-methyl-1-pentene was 4%.

The gas chromatography tests were conducted under such conditions that the column used was 2 m. in length and had been packed with the solid phase of a carrier of a diatomaceous earth system (Produced by Nippon Chromato Industrial Co.,) and with the liquid phase of 20% Squarane (2,6,10,15,19,23 - hexamethyltetracosane produced by Nippon Chromato Industrial Co.,), the temperature used was 65°C. and the carrier gas used was hydrogen. The quantitative determination was conducted by use of a calibration curve which had been formed previously.

EXAMPLE 2

Using the same reagent as in Example 1, the reaction was carried out in the same manner as in Example 1 except that 3.0 g. of N-methylpiperidine was used and the reaction time was 2.6 hours. As a result, the conversion of propylene was determined to be 63%, and the selectivity for 4-methyl-1-pentene was 91%.

EXAMPLE 3

In the same manner as in Example 1, 2.0 g. of potassium, 3.2 g. of copper powder, 3.1 g. of triethylamine, 70 ml. of heptane and 60 g. of propylene were used and reacted at 180°C. for 2.2 hours. As a result, the conversion of propylene was determined to be 57% and the selectivity for 4-methyl-1-pentene was 88%.

EXAMPLE 4

In the same manner as in Example 1, 2.0 g. of potassium, 3.2 g. of copper powder, 5.3 g. of tributylamine, 70 ml. of heptane and 68 g. of propylene were used and reacted at 180°C. for 2.5 hours. As a result, the conversion of propylene was determined to be 47% and the selectivity for 4-methyl-1-pentene was 91%.

EXAMPLE 5

In the same manner as in Example 1, 2.0 g. of potassium, 3.2 g. of copper powder, 8.0 g. of tripropylamine, 70 ml. of heptane and 77 g. of propylene were used and reacted at 180°C. for 4.8 hours. As a result, the conversion of propylene was determined to be 51 % and the selectivity for 4-methyl-1-pentene was 89%.

EXAMPLE 6

In the same manner as in Example 1, 2.0 g. of potassium, 3.2 g. of copper powder, 3.0 g. of trihexylamine, 70 ml. of heptane and 68 g. of propylene were used and reacted at 180°C. for 2.8 hours. As a result, the conversion of propylene was determined to be 45 % and the selectivity for 4-methyl-1-pentene was 90%.

EXAMPLE 7

In the same manner as in Example 1, 2.0 g. of potassium, 3.2 g. of copper powder, 2.0 g. trioctylamine, 70 ml. of heptane and 68 g. of propylene were used and reacted at 180°C. for 4 hours. As a result, the conversion of propylene was determined to be 55 % and the selectivity for 4-methyl-1-pentene was 90 %.

EXAMPLE 8

In the same manner as in Example 1, 2.0 g. of potassium, 3.2 g. of copper powder, 0.6 g. of N,N,N',N'-tetramethylethylenediamine, 70 ml. of heptane and 67 g. of propylene were used and reacted at 180°C. for 4.5 hours. As a result, the conversion of propylene was determind to be 45 % and the selectivity for 4-methyl-1-pentene was 92 %.

What is claimed is:

1. A process for producing 4-methyl-1-pentene, which comprises dimerizing propylene in the presence of a catalyst composed of (a) potassium, (b) copper and (c) from 0.1 to 5 moles per mole of potassium of an aliphatic tertiary amine having 3 to 30 carbon atoms.

2. A process for producing 4-methyl-1-pentene as claimed in claim 1, wherein the aliphatic tertiary amine is selected from the group consisting of trimethylamine, triethylamine, tripropylamine, tributylamine, trihexylamine, trioctylamine, N-methylpyrrolidine, N-methylpiperidine, N,N,N',N'-tetramethyl-ethylenediamine and 1,4-diazabicyclo(2.2.2) octane.

3. A process for producing 4-methyl-1-pentene as claimed in claim 1, wherein the dimerization is carried out in an inert gas atmosphere at 150° – 200°C. in the substantial absence of oxygen and water.

* * * * *

UNITED STATES PATENT OFFICE
CERTIFICATE OF CORRECTION

Patent No. 3,950,450          Dated April 13, 1976

Inventor(s) HARUKICHI HASHIMOTO ET AL

It is certified that error appears in the above-identified patent and that said Letters Patent are hereby corrected as shown below:

Page 1, first line under the ABSTRACT OF THE DISCLOSURE, change "present" to --presence--.

Column 1, line 35, change "No. 11871/72" to --No. 11870/72--.

Column 2, line 41, change "1-herene" to --1-hexene--.

Signed and Sealed this

Tenth Day of August 1976

[SEAL]

Attest:

RUTH C. MASON
Attesting Officer

C. MARSHALL DANN
Commissioner of Patents and Trademarks